United States Patent
Sharma et al.

(10) Patent No.: US 11,642,078 B2
(45) Date of Patent: May 9, 2023

(54) INTERVENTION FOR HEART FAILURE MANAGEMENT

(71) Applicant: Medtronic, Inc., Minneapolis, MN (US)

(72) Inventors: Vinod Sharma, Maple Grove, MN (US); Eduardo N. Warman, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 209 days.

(21) Appl. No.: 17/111,185

(22) Filed: Dec. 3, 2020

(65) Prior Publication Data

US 2021/0169407 A1 Jun. 10, 2021

Related U.S. Application Data

(60) Provisional application No. 62/944,116, filed on Dec. 5, 2019.

(51) Int. Cl.
| | | |
|---|---|---|
| A61B 5/00 | (2006.01) | |
| A61B 5/021 | (2006.01) | |
| A61B 5/024 | (2006.01) | |
| A61B 5/20 | (2006.01) | |

(52) U.S. Cl.
CPC ............ *A61B 5/4839* (2013.01); *A61B 5/021* (2013.01); *A61B 5/02405* (2013.01); *A61B 5/201* (2013.01); *A61B 5/4848* (2013.01); *A61B 5/4857* (2013.01); *A61B 5/746* (2013.01)

(58) Field of Classification Search
CPC ..... A61B 5/021; A61B 5/02405; A61B 5/201; A61B 5/29; A61B 5/361; A61B 5/4836; A61B 5/4839; A61B 5/4848; A61B 5/4857; A61B 5/746; A61N 1/362; A61N 1/3756; A61N 1/3904; A61N 1/3956
See application file for complete search history.

(56) References Cited

U.S. PATENT DOCUMENTS

| | | | |
|---|---|---|---|
| 9,713,701 B2 * | 7/2017 | Sarkar | A61B 5/1118 |
| 10,368,774 B2 | 8/2019 | Sharma et al. | |
| 2005/0136385 A1 * | 6/2005 | Mann | A61N 1/025 434/320 |
| 2009/0062730 A1 * | 3/2009 | Woo | A61M 5/1723 604/66 |
| 2010/0113945 A1 * | 5/2010 | Ryan | A61B 5/053 600/486 |

(Continued)

OTHER PUBLICATIONS

International Search Report and Written Opinion from PCT Application No. PCT/US2020/063239 dated Mar. 3, 2021, 8 pages.

(Continued)

*Primary Examiner* — Brian T Gedeon
(74) *Attorney, Agent, or Firm* — Mueting Raasch Group

(57) ABSTRACT

A method for heart failure management may include volume overload intervention in response to sensor-based parameters indicating volume overload. The method may include administering non-volume overload intervention in response to the sensor-based parameters not indicating volume overload. Volume overload may be determined based on monitoring sensor-based parameters. Sensor-based parameters may be monitored in response to receiving an alert indicative of a worsening heart failure score or status for a patient.

20 Claims, 6 Drawing Sheets

(56) References Cited

U.S. PATENT DOCUMENTS

| | | |
|---|---|---|
| 2016/0129260 A1 | 5/2016 | Mann et al. |
| 2016/0171174 A1 | 6/2016 | Murata |
| 2016/0310031 A1 | 10/2016 | Sarkar |
| 2017/0245794 A1 | 8/2017 | Sharma et al. |
| 2019/0069851 A1 | 3/2019 | Sharma et al. |
| 2019/0125273 A1 | 5/2019 | Sharma et al. |
| 2019/0329043 A1 | 10/2019 | Sharma |
| 2019/0336077 A1 | 11/2019 | Kuhn et al. |
| 2020/0353250 A1 | 11/2020 | Haddad et al. |

OTHER PUBLICATIONS

International Preliminary Report on Patentability from PCT Application No. PCT/US2020/063239 dated Jun. 7, 2022, 6 pages.

* cited by examiner

INTERVENTION FOR HEART FAILURE MANAGEMENT

The present application claims the benefit of U.S. Provisional Application No. 62/944,116, filed Dec. 5, 2019, which is incorporated herein by reference in its entirety.

The present technology is generally related to medical treatment. In particular, the present technology is related to managing treatment for heart failure or other chronic conditions.

As one example of a chronic condition, chronic heart failure (HF) occurs when a heart of a patient is unable to consistently pump blood at an adequate rate in response to the filling pressure. To improve the ability of the heart to pump blood, congestive heart failure patients may be given therapy. In some cases, therapy may be provided by implantable medical devices (IMDs) such as implantable cardioverter defibrillators (ICDs), cardiovascular implantable electronic devices (CIEDs), pacemakers, and cardiac resynchronization therapy (CRT) devices that, in some cases, include defibrillation capability (CRT-D devices).

Despite using IMDs to improve heart function, some HF patients may experience worsening HF. Some systems are capable of identifying patients at risk of worsening HF, for example, based on data detected by IMDs. One exemplary system relates to U.S. Pat. No. 9,713,701 to Sarkar et al. that is capable of generating alerts for a patient to seek medical treatment in response to detected information. For example, a medical device may detect worsening heart failure in the patient based on a diagnostic parameter. Upon detecting worsening heart failure, the medical device may, for example, provide an alert.

Once patients at risk are identified with an alert, some patients may benefit from hospitalization, while others may benefit from specific interventions. Some existing systems can provide guidance using diuretics. Effective actions guided by diagnostics have been difficult to determine to provide more complete HF management.

SUMMARY

The techniques of this disclosure generally relate to device diagnostics guided intervention for complete HF management. The guided intervention techniques leverage various device diagnostics and optionally external diagnostics that could be available using a care management system. The techniques clearly delineate treatment changes and other actions that can be taken in response to changes in the measured diagnostics. In particular, the techniques may be used to administer treatments that include one or more drugs to provide complete HF management for a patient. Administered treatments may include effective titrations of these drugs. The techniques may also provide guidance as to whether the patient should seek medical attention from a clinician or hospital.

In one aspect, the present disclosure provides a method for heart failure management that includes receiving an alert indicative of a worsening heart failure score or status for a patient; monitoring sensor-based parameters in response to receiving the alert; determining whether the monitored sensor-based parameters indicate volume overload; administering volume overload intervention in response to the monitored sensor-based parameters indicating volume overload; and administering non-volume overload intervention in response to the monitored sensor-based parameters not indicating volume overload.

In another aspect, the present disclosure provides a heart failure management system. The system includes one or more sensors to measure one or more sensor-based parameters selected from: impedance, resting heartrate, heartrate variability, nighttime heart rate, atrial fibrillation, rapid ventricular rate, activity, systolic blood pressure, and oxygen perfusion, cardiac output, and cardiac index. The system also includes processing circuitry operably coupled to the one or more sensors, the processing circuitry configured to: monitor sensor-based parameters in response to receiving an alert indicative of a worsening heart failure score or status for a patient; determine whether the monitored sensor-based parameters indicate volume overload; administer volume overload intervention in response to the sensor-based parameters indicating volume overload; and administer non-volume overload intervention in response to the monitored sensor-based parameters not indicating volume overload.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
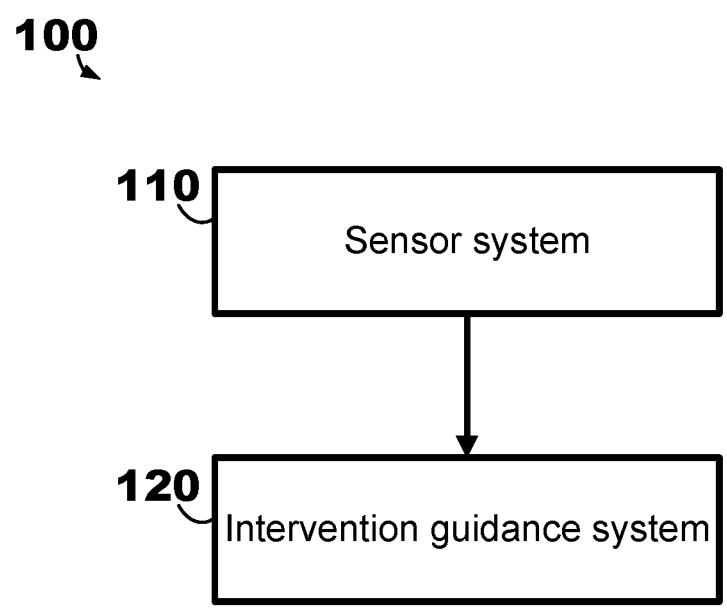
FIG. 1 is a block diagram that illustrates one example of a treatment management system according to the present disclosure.

The techniques of this disclosure provide device diagnostics guided intervention for complete HF management. The guided intervention techniques leverage various device diagnostics and optionally external diagnostics that could be available using a care management system. The techniques clearly delineate treatment changes and other actions that can be taken in response to changes in the measured diagnostics. In particular, the techniques may be used to administer treatments that include one or more drugs to provide complete HF management for a patient. Administered treatments may include effective titrations of these drugs. The techniques may also provide guidance as to whether the patient should seek medical attention from a clinician or hospital.

As used herein, the term "administer" refers to guiding or providing of a treatment or intervention, which may include using drugs, pacing, or other techniques. For example, administering diuretic intervention may include providing guidance to a clinician to provide a diuretic drug or providing the diuretic drug to the patient.

As used herein, the term "or" is generally employed in its inclusive sense, for example, to mean "and/or" unless the context clearly dictates otherwise. The term "and/or" means one or all the listed elements or a combination of at least two of the listed elements.

The phrases "at least one of" and "one or more of" followed by a list conjoined by "and" or "or" generally refers to any one of the items in the list and any Reference will now be made to the drawings, which depict one or more aspects described in this disclosure. However, it will be understood that other aspects not depicted in the drawings fall within the scope of this disclosure. Like numbers used in the figures refer to like components, steps, and the like. However, it will be understood that the use of a reference character to refer to an element in a given figure is not intended to limit the element in another figure labeled with the same reference character. In addition, the use of different reference characters to refer to elements in different figures is not intended to indicate that the differently referenced elements cannot be the same or similar.

FIG. 1 is a block diagram that illustrates one example of an HF management system 100 that may be used in providing complete HF management. The system 100 may include one or more sensors in a sensor system 110 and may include processing circuitry in an intervention guidance system 120. In particular, the system 100 may be used to administer treatments that include one or more drugs, such as diuretics, betablockers, angiotensin converting enzyme inhibitor (ACEi), angiotensin receptor blocker (ARB), and a combination of neprilysin inhibitor and ARB (Sacubitril/ valsartan), among others, to provide complete HF management for a patient.

The system 100 may leverage various device diagnostics and optionally external diagnostics that could be available using a care management system. The sensor system 110 may be used to provide these device diagnostics and optional external diagnostics related to the patient. The device diagnostics and optional external diagnostics may also be collectively described as diagnostics, diagnostic parameters, or measured diagnostics. Various types of sensors may be included in the sensor system 110, such as patient implantable sensors, patient wearable sensors, external sensors not worn by the patient (such as smartphones or lab equipment), and graphical or audible user interfaces to accept input from users (such as the patient or the clinician). Examples of patient implantable sensors, patient wearable sensors, and external sensors include, but are not limited to, electrical contacts (or electrodes), biochemical sensors, motion sensors (such as 3-axis accelerometers or other inertial measurement units), piezoelectric sensors, microphones, temperature sensor, and optical sensors. Furthermore, external sensors may include weight scales and pressure sensors.

A patient implantable sensor may be included in any suitable IMD. Non-limiting examples of IMDs include leaded or leadless pacemakers, which may or may not be intracardiac, implantable cardioverter defibrillators (ICDs), which may or may not be extravascular (EVICDs), cardiac resynchronization therapy pacemakers (CRT-Ps), cardiac resynchronization therapy defibrillators (CRT-Ds), and insertable cardiac monitors (ICMs, such as Reveal LINQ available from Medtronic plc of Dublin, Ireland). One example of an ICM is described with respect to U.S. Publication No. 2016/0310031, filed Apr. 20, 2016, which is incorporated by reference in its entirety.

Patient wearable sensors may be included in any suitable wearable device. Non-limiting examples of patient wearable devices include heartrate monitors, smart watches, pulse oximeters, patches to monitor vitals and activity, hearing aids with capability to detect vitals and activity (vitals such as core temperature), and pendant-like devices to measure activity.

An external sensor not worn by the patient may be used to provide data input into the intervention guidance system 120 and optionally included in the sensor system 110. Some external sensors may be described as lab equipment or tests. Some external sensors may be incorporated into external devices. Non-limiting examples of external devices include smartphones, tablets, personal computers, treatment dispensers, weight scales, blood pressure cuffs, beds integrated with sensors, or other furniture integrated with sensors.

Patient data may be obtained in a variety of ways by the sensor system 110. For example, a patient may directly convey health data to medical personnel during an office visit with a clinician, which is input into a user interface. Some data may be automatically generated by sensors and sent over the internet to the intervention guidance system 120. For example, electronic weight scales may be configured to weigh a patient and automatically transmit the patient weight data to the intervention guidance system 120.

The device diagnostics and optional external diagnostics may include any suitable measurements and parameters that facilitate complete HF management. Non-limiting examples of diagnostics include thoracic impedance, heartrate (HR), atrial-to-atrial (AA) intervals to detect atrial fibrillation (AF), ventricular rate during AF or rapid ventricular rate (RVR), daytime resting heartrate (which may be derived from a ventricular RR interval, wherein the R is the R of the QRS complex; may be measured supine), nighttime heartrate (NHR), heartrate variability (HRV), activity, cough, heart sounds (such as the S3 heart sound), patient weight, stroke volume (SV), cardiac output (CO), cardiac index (CI), filling pressure, and systolic blood pressure (BP), creatinine or estimated glomerular filtration rate (eGFR), potassium (K+), and oxygen perfusion.

In general, one or more of the diagnostics may be device diagnostics captured by an IMD or patient wearable device. In some embodiments, one or more of the diagnostics may be captured by an external sensor or by user input.

Thoracic impedance may be measured using electrodes, for example, on an IMD and an intracardiac lead. For example, a housing-based electrode on the IMD housing (which may be described as a can) and an electrode on an RV coil lead may be used. A decreasing thoracic impedance may be used to indicate increasing cardiac preload and fluid accumulation.

HR or daytime resting heartrate may be measured using electrodes, for example, on an IMD (such as a housing-based electrode), an intracardiac lead, or an optical sensor on a patient wearable sensor. Elevated HR may be used as an indication of high HF risk. Elevated HR may also be used to indicate whether a patient has room for up-titration of medications, such as beta blockers. AA intervals may be measured using electrodes on, for example, an IMD (such as a housing-based electrode), an intracardiac lead, or an optical sensor on a patient wearable sensor. AA intervals may be used to distinguish between an atrial rhythm (such as AF) and a sinus rhythm. In some cases, AF may lead to worsening HF.

NHR may be measured using electrodes, for example, on an IMD (such as a housing-based electrode), an intracardiac lead, or an optical sensor on a patient wearable sensor. Elevated NHR may indicate elevated autonomic tone and may also be used as an indication of high HF risk.

HRV may be measured using electrodes, for example, on an IMD (such as a housing-based electrode), an intracardiac lead, or an optical sensor on a patient wearable sensor. Decreased HRV may be used to indicate elevated sympathetic tone and autonomic imbalance. Decreased HRV may be associated with elevated HR.

Activity may be measured using a motion sensor, such as an inertial measurement unit (IMU), in the IMD or patient wearable sensor. Activity may be used to indicate overall functional status of the patient. For example, decrease in activity may occur as patient's risk of worsening heart failure increases.

Heart sounds, such as the S3 heart sound, may be measured using, for example, an accelerometer, a piezoelectric sensor, or microphone on an IMD. The presence of the S3 heart sound may be used to indicate elevated pulmonary atria pressure and may also be used to indicate increased risk of worsening HF.

Patient weight may be measured, for example, using a weight scale. Increased weight may be used to indicate fluid accumulation.

SV may be measured, for example, indirectly using an optical sensor and tissue oxygen sensor on an IMD or patient wearable sensor. Decreased SV may be used to indicate worsening HF.

Oxygen perfusion may be measured, for example, using an optical sensor on an IMD or patient wearable sensor. Decreased oxygen perfusion may be used to indicate worsening HF. Oxygen perfusion may be associated with, or correlated with, CO.

CO may be determined, for example, based on SV and HR. CO may be calculated by multiplying SV and HR. CO may be used to indicate worsening HF.

CI may be determined, for example, based on CO normalized to a patient's body surface area. CI may be used to indicate worsening HF. In some embodiments, CI may be used instead of CO, for example, when the patient's body surface area is known.

Filling pressure may be measured using a pressure sensor located, for example, in the LA or in the pulmonary artery. Elevated filling pressure may be used to indicate worsening HF.

SBP may be measured, for example, using a wearable cuff. In general, SBP may be used to guide intervention. Elevated SBP may be used to indicate that certain interventions for worsening HF may be used. SBP lower than a threshold may be used to indicate that certain interventions for worsening HF may be excluded.

Ventricular rate during AF or RVR may be measured using electrodes, for example, on an IMD (such as a housing-based electrode), an intracardiac lead, or an optical sensor on a patient wearable sensor. RVR may be used to indicate worsening HF.

Creatinine or eGFR may be measured, for example, in the lab using lab equipment or using an IMD. Elevated creatinine or eGFR may be used to indicate poor renal function. Creatinine or eGFR may be used to guide intervention. In some embodiments, elevated creatinine or eGFR may be used to indicate that certain interventions, such as diuretics, may be excluded.

Potassium (K+) may be measured, for example, in the lab using lab equipment or using an IMD. Potassium may be used to guide intervention. In some embodiments, elevated potassium may be used to indicate that certain interventions, such as potassium-sparing spironolactone, may be excluded.

The CI may be used additionally or alternatively to the CO. In general, CI is CO normalized to body surface area.

An accelerometer and/or piezo electric sensor can be used to measure heart sounds, such as the S3 and S4 heart sounds. Heart sounds may emerge as the patient gains fluid and heart failure begins to worsen.

In general, heart sounds are associated with mechanical vibrations of a patient's heart and the flow of blood through the heart valves and, thus, may be highly correlated with pressure gradients across heart valves and blood pressure. Heart sounds may be not only due to vibrations of and pressure within the heart, but may also be due to the entire cardiohemic system, e.g., blood, heart, great arteries, etc. Heart sounds may recur with each cardiac cycle and are separated and classified according to the activity associated with the vibration.

The first heart sound is referred to as "S1," and can be thought of as the vibration sound made by the heart during closure of the atrioventricular, or AV, valves, i.e., the mitral valve and tricuspid valve. The S1 sound can sometimes be broken down into the M1 sound component, from the closing of the mitral valve, and the T1 sound component, from the closing of the tricuspid valve. The second heart sound is referred to as "S2," and results from the closure of the semilunar valves, i.e., the pulmonary and aortic valves. The S2 heart sound can be thought of as marking the beginning of diastole. The S2 sound can also be broken down into component parts. The P2 sound component is from the closing of the pulmonary valve and the A2 sound component is from the closing of the aortic valve. The third and fourth heart sounds are referred to as "S3" and "S4," respectively, and can be conceptualized as related to filling of the ventricles during diastole. S3 is due to rapid filling of the ventricles and can occur when the ventricular wall is not relaxed when a large volume of blood flows into the ventricles from the atria. S4 is caused by blood rapidly filling into the ventricles from the atria due to atrial contraction.

Diagnostics may be updated at any suitable rate to monitor the patient's condition. In some embodiments, diagnostics may be updated for purposes of HF management every day. In other embodiments, diagnostics may be updated twice per day, for example, once during the day and once during the night. In general, diagnostics are updated at least once every two days.

The intervention guidance system 120 may receive various measured diagnostics from the sensor system 110 to clearly delineate treatment changes and other actions that can be taken in response to changes in the measured diagnostics. In some embodiments, the data from the sensor system 110 may be provided in a raw data format (such as in the form of sensor signals) or provided in a refined or digital format more easily transmitted between systems.

Administered treatments may include effective titrations of various drugs. The techniques may also provide guidance as to whether the patient should seek medical attention from a clinician or hospital.

In general, the diagnostic measurements and the functionality of the intervention guidance system may be carried out using processing circuitry. In some embodiments, a computer-readable medium may include instructions stored thereon. The instructions, when executed, may cause the system 100 to perform the measurements and functionality described herein.

The system 100 may include processing resources that are accessible over the internet or another type of network. One or more sensors of the sensor system 110 may be operably connected to the intervention guidance system 120 through a network.

In some embodiments, the intervention guidance system 120 may be part of, or be connected to, a remote care management system, such as CARELINK available from Medtronic plc of Dublin, Ireland, for example, through the internet. Processing circuitry to carry out some or all of the functionality of the intervention guidance system 120 may be located in the remote care management system.

In some embodiments, some or all the functionality of system 100 may be carried out using a clinician device or patient device, such as a smartphone, a tablet, or other patient-controlled device.

Generally, processing circuitry of the intervention guidance system 120 may be coupled to one or more sensors of the sensor system 110 and configured to monitor diagnostics, which may be in response to receiving an alert indicating a possibly worsening risk of HF, determine whether the patient is experiencing volume overload, and administer the appropriate intervention. In particular, the processing circuitry may be configured to monitor sensor-based parameters in response to receiving an alert indicative of heart failure of a patient's heart. The processing circuitry may also be configured to determine whether the monitored sensor-based parameters indicate volume overload. The processing circuitry may also be configured to administer volume overload intervention in response to the monitored sensor-based parameters indicating volume overload. Further, the processing circuitry may be configured to administer non-volume overload intervention in response to the monitored sensor-based parameters not indicating volume overload.

In some embodiments, the sensor system 110 may be used to measure a pulmonary artery (PA) pressure, which may be used to indicate elevated HF risk. An alert may be generated based on the elevated HF risk. The intervention guidance system 120 may be used to guide intervention in response to the alert.

Figure 2:
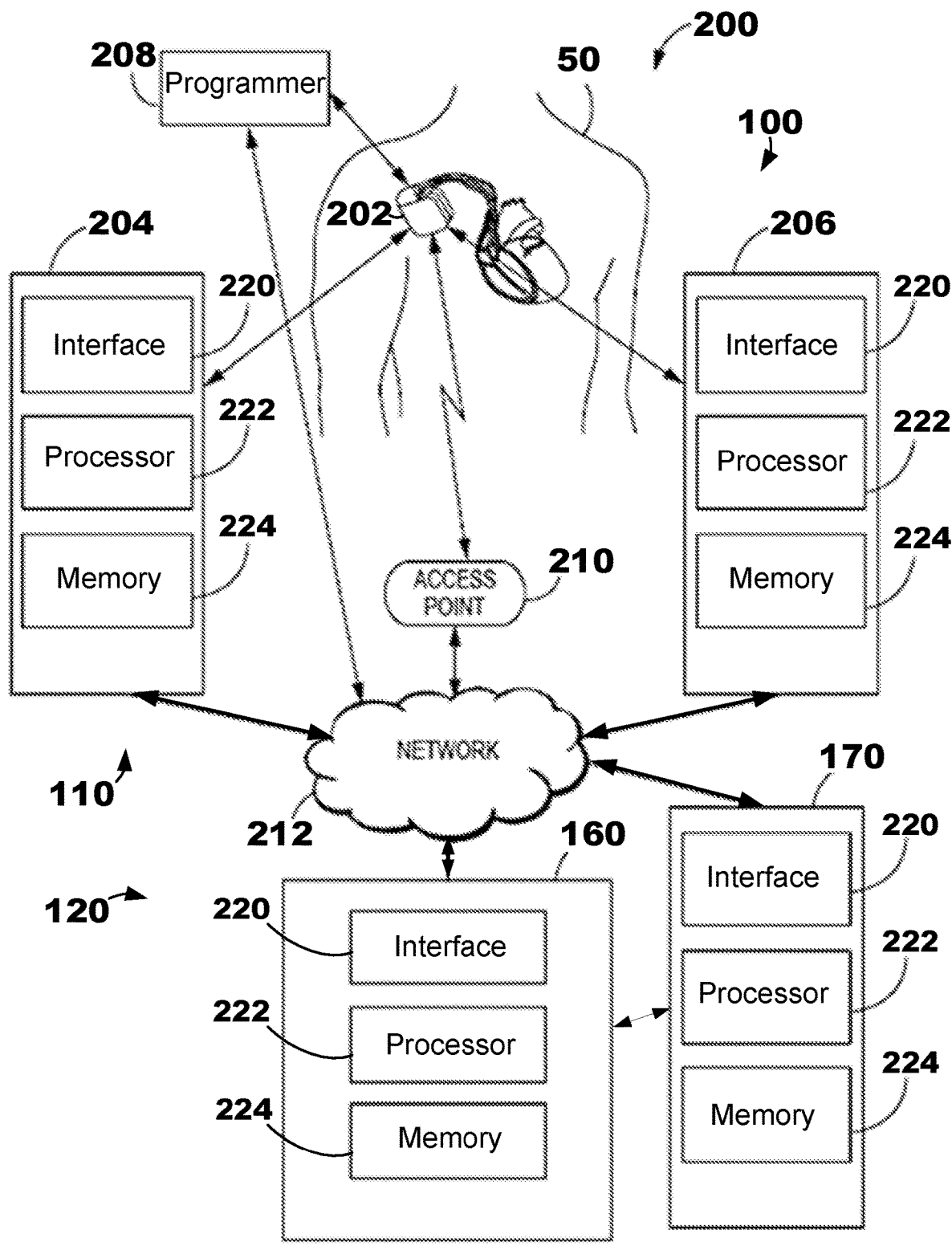
FIG. 2 is a conceptual diagram that illustrates one example of an environment usable with the treatment management system of FIG. 1.

FIG. 2 is a conceptual diagram that illustrates one example of an environment usable with the HF management system 100 of FIG. 1. As shown, an environment 200 for use with the system 100 may include the body of a patient 50.

Any suitable elements, or devices, may be used to implement the system 100. Non-limiting examples of techniques and systems that may be included and used with the system 100 are described in U.S. patent application Ser. No. 15/402,839, filed on Jan. 10, 2017, published as U.S. Patent Publication No. 2017/0245794, U.S. patent application Ser. No. 16/394,942, filed Apr. 25, 2019, published as U.S. Patent Publication No. 2019/0329043, U.S. patent application Ser. No. 16/863,340, filed Apr. 30, 2020, published as U.S. Patent Publication No. 2020/0353250, which are incorporated by reference in their entireties. In some embodiments, various elements may be used to intervene and provide one or more drugs, such as diuretics.

The sensor system 110 may include any suitable device having a sensor for acquiring patient data. In some embodiments, the sensor system 110 may include an IMD 202 having a patient implantable sensor, a patient wearable device 204 having a patient wearable sensor, and an external device 206 having an external sensor.

Various types of patient implantable sensors may be used to operably couple to circuitry of the IMD 202 for use in providing patient data. One or more patient implantable sensors may be incorporated into or operably coupled to various IMDs 202, such as pacemakers, ICDs, EVICDs, CRT-Ps, CRT-Ds, and ICMs.

Various types of patient wearable sensors may be used to operably couple to circuitry of the patient wearable device 204 for use in providing patient data. One or more patient wearable sensors may be incorporated into, or operably coupled to, various patient wearable devices 204.

Various types of external sensors may be used to operably couple to circuitry of the external device 206 for use in providing patient data. One or more external sensors may be incorporated into, or operably coupled to, various external devices 206.

The various sensors of the sensor system 110 may be used in various ways to provide patient data. In one example, a pressure sensor or accelerometer may be embedded into furniture, such as a couch or bed, and used to provide respiratory data and heart rate.

In another example, an electrical sensor on the IMD 202 or a patient wearable device 204 may include an electrical sensor used to monitor electrical activity to provide, for example, an electrocardiogram (ECG), an impedance value, respiration data, or a fluid level.

In another example, a 3-axes accelerometer can be used to measure patient's activity, changes in gait pattern, and frailty metrics (e.g., time required to get up from a couch and walk certain distance). An accelerometer and/or piezo electric sensor can be used to measure S3 heart sounds (these sounds may emerge as a patient gains fluid and their heart failure begins to worsen).

One or more devices of the sensor system 110 may be operably coupled to a programmer 208 or an access point 210. The programmer 208 or access point 210 may be wirelessly connected or connected by wire to one or more devices. For example, the programmer 208 and the access point 210 may be wirelessly connected to the IMD 202 to transmit and receive data. In turn, the programmer 208 and the access point 210 may be operably coupled to a network 212, which may include a local network, wide area network, or the internet, to further transmit and receive data.

Some or all the intervention guidance system 120 may be part of one or more devices of the sensor system 110, such as the IMD 202, the patient wearable device 204, and the external device 206. In some embodiments, the intervention guidance system 120 may include an optional remote system 160 and an optional treatment delivery system 170. The sensor system 110 may be operably coupled to the remote system 160 and the treatment delivery system 170, for example, through the network 212. In some embodiments, some or all determinations to generate a risk score or status or to guide intervention may be made in the cloud using cloud computing systems.

The treatment delivery system 170 may include any suitable device for administering treatment for the patient. In some embodiments, the treatment delivery system 170 may include a drug dispenser to contain one or more drugs, an automated subcutaneous (SubQ) or fully implanted treatment pump, an intravenous or intraperitoneal line, or a graphical or audible user interface to provide treatment information to the patient. The treatment delivery system 170 may be operably coupled to the remote system 160.

One or more systems of the system 100 may include one or more computing devices having a controller or processing circuitry, which may include a data communication interface 220, a processor 222, and a memory 224. The functions of the processing circuitry may be performed by hardware and/or as computer instructions on a non-transient computer readable storage medium.

Processor 222 may include any one or more of a microprocessor, a microcontroller, a digital signal processor (DSP), an application specific integrated circuit (ASIC), a field-programmable gate array (FPGA), and/or equivalent discrete or integrated logic circuitry. In some examples, processors 222 may include multiple components, such as any combination of one or more microprocessors, one or more controllers, one or more DSPs, one or more ASICs, and/or one or more FPGAs, as well as other discrete or integrated logic circuitry. The functions attributed to controllers or processors 222 herein may be embodied as software, firmware, hardware, or any combination thereof. While described herein as a processor-based system, an alternative controller could utilize other components such as relays and timers to achieve the desired results, either alone or in combination with a microprocessor-based system.

In one or more embodiments, the exemplary systems, methods, techniques, and other related functionality may be implemented using one or more computer programs using a computing apparatus, which may include one or more processors 222 and/or memory 224. Program code and/or logic described herein may be applied to input data/information using the data communication interface 220 to perform functionality described herein and generate desired output data/information. The output data/information may be applied as an input to one or more other devices and/or methods as described herein or as would be applied in a known fashion using the data communication interface 220. In view of the above, it will be readily apparent that the controller or processor functionality as described herein may be implemented in any manner known to one skilled in the art having the benefit of this disclosure.

The network 212 may generally be used to transmit information or data between some or call devices of the system 100 to make determinations regarding intervention. Some information or data may also be used to inform the clinician about the patient 50, for example, using the remote system 160, which may include remote care management functionality.

A wireless connection may be employed by one or more devices of the system 100. In one example, the patent implantable device 202, the patient wearable device 204, the external device 206, the programmer 208, the access point 210, the remote system 160, and the treatment delivery system 170 are interconnected, and able to communicate with each other, directly or indirectly through the network 212.

Various data communication interfaces 220 may also include user interfaces. In some embodiments, one or more data communication interfaces 220 of the system 100 include input devices, such as touchscreens, keyboards, mice, microphones, sensors for weight, etc., or output devices, such as graphical or audible user interfaces, printers, or other suitable means.

Various memory 224 may include volatile, non-volatile, magnetic, optical, or electrical media, such as a random-access memory (RAM), read-only memory (ROM), non-volatile RAM (NVRAM), electrically-erasable programmable ROM (EEPROM), flash memory, or any other digital or analog media. In general, the memory 224 may store data, such as diagnostics.

The system 120 may send a request to a device of the sensor system 110, such as IMD 202. The IMD 202 may provide diagnostics, such as absolute intrathoracic impedance that may be indicative of hypervolemia or hypovolemia.

The patient data may be used to provide an alert or notification of the heart failure risk level by the system 100 or by an external system. The alert may be automatically transmitted, or pushed, when the heart failure risk level higher than a threshold. In addition, the alert may be a notification to a physician of the risk level and/or an instruction to patient 50 to seek medical treatment (e.g., testing to confirm worsening HF, etc.). In some embodiments, the threshold may be set for the alert to indicate that the patient should seek clinical or outpatient care. In some embodiments, a second threshold may be set for the alert to indicate that the patient should seek hospitalization. In response to receiving the alert, a user interface may display the alert to the physician regarding the risk level or present an instruction to patient 50 to drive an intervention or to seek medical treatment.

Access point 210 may include a device that connects to network 112 via any of a variety of connections. In other examples, access point 210 may be coupled to network 112 through different forms of connections, including wired or wireless connections. In some examples, access point 210 may be co-located with patient 50 and may include one or more programming units and/or computing devices (e.g., one or more monitoring units) that may perform various functions and operations described herein.

In another example, access point 210 may be an ICM device co-located within the patient and configured to sense, record and transmit data to network 112. Alternatively, a wearable patch or other wearable device available may be configured for monitoring attached to or adjacent to the skin of the patient. In another example, access point 210 may include a home-monitoring unit that is located near the patient 50 and may monitor the activity of the IMD 202.

The intervention guidance system 120 may include or be part of a centralized communication center staffed by one or more skilled nurses and an established workflow to manage/treat patients on a spectrum of episode severity (e.g., decompensated HF patient with hypotension versus normal blood pressure). The intervention guidance system 120 may be configured to perform complex computations for a large group of patients and may provide secure storage in memory for archival of information (e.g., patient metric data, heart failure risk levels, weight, blood pressure, etc.) that has been collected and generated from the sensor system 110.

Figure 3:
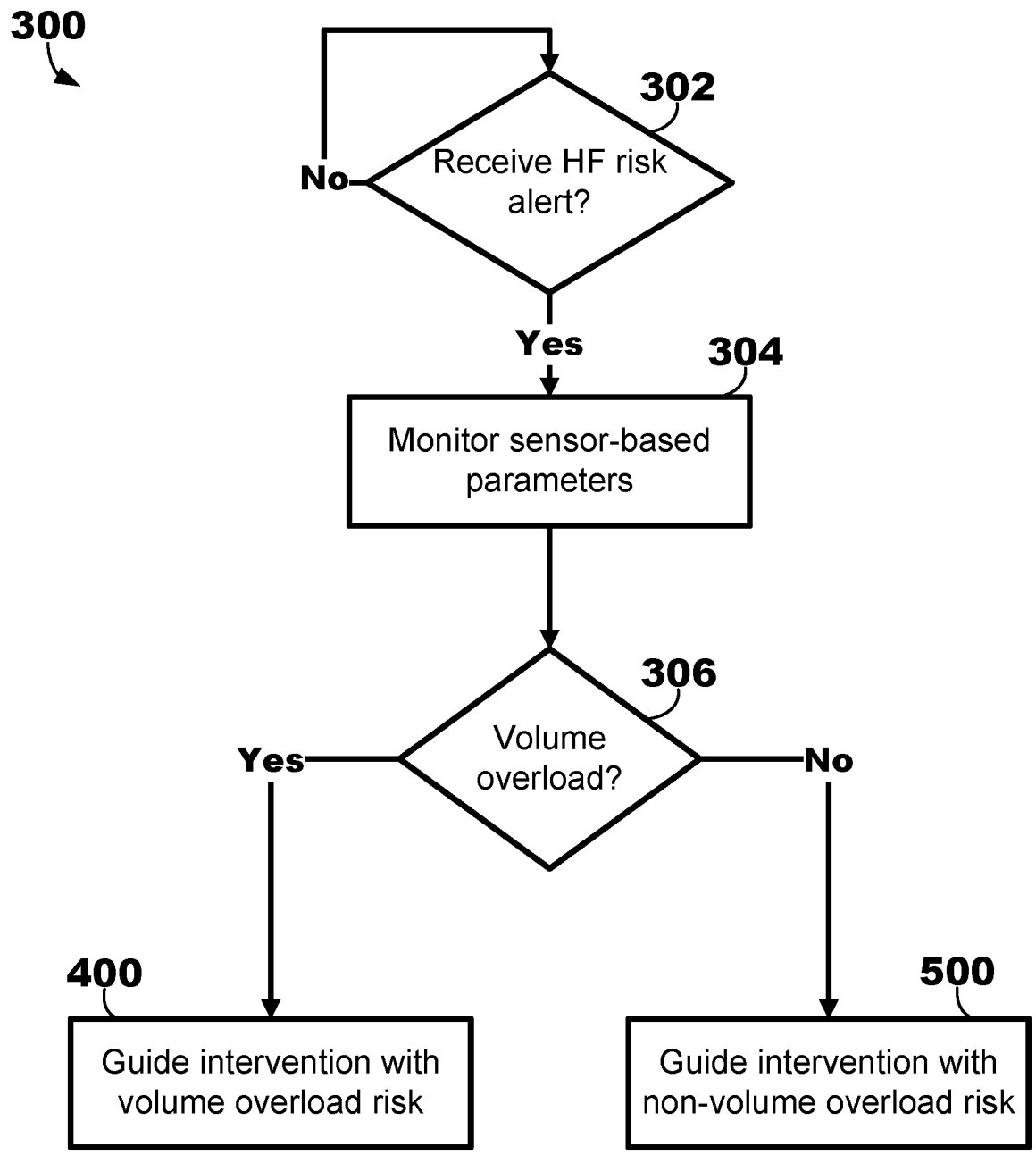
FIG. 3 is a flow diagram that illustrates one example of a method of guiding intervention based on volume overload risk usable with the treatment management system of FIG. 1 or in the environment of FIG. 2.

FIG. 3 shows one example of a method 300 of guiding intervention based on volume overload risk usable with the treatment management system 100 or in the environment 200. The method 300 may include determining whether a HF risk alert has been received 302, for example, by the system 100. The heart failure risk alert may indicate whether the patient is at risk of worsening HF. The risk of worsening HF may be described as a worsening HF score or status (e.g., low, medium, high).

The worsening HF status may be determined based on an HF risk score. HF risk scores and statuses can be calculated in a number of ways known to a person of skilled art having the benefit of this disclosure. Examples of calculating risk scores, or risk statuses, are described in U.S. Patent Publication No. 2019/0125273, filed Apr. 26, 2018, and U.S. Patent Publication No. 2019/0069851, filed Aug. 31, 2018, which are incorporated by reference in their entireties.

As illustrated, in response to not receiving a HF risk alert, the method 300 may continue to monitor, or repeatedly check, whether a HF risk alert has been received 302. The HF risk alert may be generated by the system 100 or may be provided to the system 100 from another system. The HF risk alert may be represented by data received by the system 100.

The method 300 may include monitoring one or more sensor-based parameters 304. As illustrated, in response to receiving a HF risk alert, the method 300 may include monitoring one or more sensor-based parameters 304. The sensor-based parameters may include one or more of the device diagnostics and optionally one or more external diagnostics. The sensor-based parameters may be determined or generated by the system 100 or may be provided to the system 100 from another system. The sensor-based parameters may be used and stored as data in the system 100.

The method 300 may include determining whether the patient has volume overload 306. Volume overload may be determined based on the sensor-based parameters. As illustrated, in response to monitoring the sensor-based parameters, the method 300 may include determining whether the patient has volume overload 306.

Volume overload may be defined in any suitable manner available to one of ordinary skill in the art having the benefit of the present disclosure. In some embodiments, volume overload may be determined by comparing sensor-based parameters to corresponding thresholds generating using population level data. Thresholds may be optimized or modified for each patient on a per-patient basis. Thresholds may be modified, for example, when too many false alerts are generated or when certain thresholds are insensitive for a specific patient. Techniques for identifying volume overload using sensor-based parameters may be described in, for example, U.S. Pat. No. 10,368,774, issued Aug. 6, 2019, which is incorporated by reference in its entirety.

In some embodiments, determining that the patient has volume overload 306 may include comparing one or more parameters to corresponding thresholds. For example, a determination that the patient has volume overload 306 may be based on at least one or more of the following parameters and corresponding thresholds: a decreased or low impedance, an increased or elevated daytime resting HR (for example, supine), a decreased or low HRV, an increased or elevated NHR, a decreased or low activity level, increased or elevated coughing, an indication of the ventricular gallop (such as detection of an S3 heart sound representing the filling of the heart), and an increased or elevated weight.

In some embodiments, determining that the patient does not have volume overload 306 may include comparing one or more parameters to corresponding thresholds. For example, a determination that the patient is at risk of worsening HF not associated with volume overload may be based on at least one of more of the following parameters and corresponding thresholds: an impedance within a target range (such as a normal range that is neither high nor low), an increased or elevated daytime resting HR (for example, supine), a decreased or low HRV, an increased or elevated NHR, a decreased or low SV, a decreased or low marker of CO (such as oxygen perfusion or CI), and a decreased or low marker of filling pressure and decreased daily activity.

The method 300 may include guiding intervention with volume overload risk 400 and may include guiding intervention with non-volume overload risk 500. As illustrated, in response to determining that the patient has volume overload 306, the method 300 may include guiding intervention with volume overload risk 400. In response to determining that the patient does not have volume overload 306, the method 300 may include guiding intervention with non-volume overload risk 500.

Guiding intervention for patients with volume overload risk 400 may include administering diuretics. Diuretics may be administered with increasing doses over a few days. In some cases, another class of drugs called nitrates may also be used in subset of patients. Nitrates may be used for patients when diuretics are not sufficient to treat patients having an indication of worsening HF and a volume overload risk.

Guiding intervention for patients with non-volume overload risk 500, or without volume overload risk, may include not increasing the administration of diuretics. In general, patients at risk of HF may be provided with some level of diuretics, which may not be increased, for example, if the risk of HF is not associated with volume overload. In some cases, diuretics may be decreased for some patients. Doses of other drugs on a more permanent basis may be made for patients having an indication of worsening HF and a non-volume overload risk.

Techniques for administering diuretics that may be used are described in U.S. patent application Ser. No. 15/402,839, filed on Jan. 10, 2017, published as U.S. Patent Publication No. 2017/0245794, U.S. patent application Ser. No. 16/393, 942, filed Apr. 25, 2019, and U.S. patent application Ser. No. 16/863,340, filed Apr. 30, 2020, which are incorporated by reference in their entireties.

Figure 4:
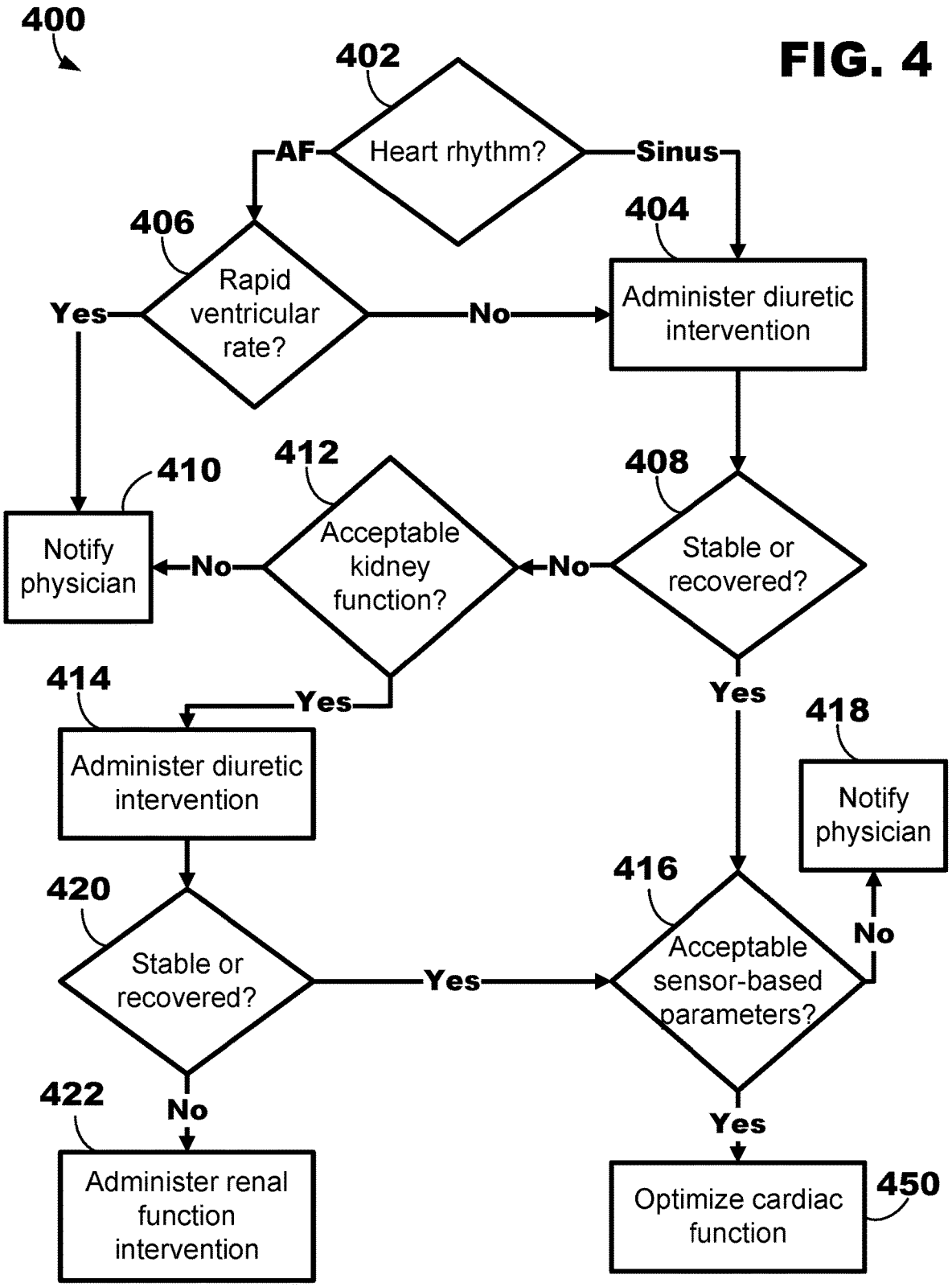
FIG. 4 shows a flow diagram that illustrates one example of a method guiding intervention with volume overload risk usable in the method of FIG. 3, with the treatment management system of FIG. 1, or in the environment of FIG. 2.

FIG. 4 shows a flow diagram that illustrates one example of the method 400 of guiding intervention with volume overload risk usable in the method 300, with the system 100, or in the environment 200. The method 400 may include determining the type, or classification, of heart rhythm of the patient 402. The heart rhythm of the patient may be determined based on sensor-based parameters determined or generated by the system 100 or may be provided to the system 100 from another system.

Any suitable technique may be used to determine the type of heart rhythm known to one of ordinary skill in the art having the benefit of the present disclosure. In some embodiments, the type of heart rhythm may be determined based on only ventricular electrogram (EGM). The ventricular EGM may be detectable using, for example, a single-chamber 1 MB. In some embodiments, the type of heart rhythm may be determined based on a ventricular EGM in combination with an atrial EGM. Using the atrial EGM may be helpful in determining whether the heart rhythm is in AF.

Diuretic intervention may be administered 404 in the method 400. As illustrated, in response to determining that the heart rhythm is a sinus rhythm 402, the method 400 may include administering diuretic intervention 404. Also, as illustrated, in response to determining that the patient does not have RVR 406, the method 400 may include administering diuretic intervention 404.

Any suitable technique may be used to administer diuretic intervention known to one of ordinary skill in the art having the benefit of the present disclosure. In some embodiments, administering diuretic intervention drugs may include prescribing or providing diuretic drugs to the patient.

Determining whether the patient has an RVR 406 may be included in the method 400. As illustrated, in response to determining that the heart rhythm is in AF 402, the method 400 may include determining whether the patient has an RVR 406. The RVR may be determined based on sensor-based parameters determined or generated by the system 100 or may be provided to the system 100 from another system.

Any suitable technique may be used to determine whether the patient has an RVR known to one of ordinary skill in the art having the benefit of the present disclosure. In some embodiments, the RVR may be determined based on comparing a ventricular rate to a threshold. In one example, RVR may be determined in response to detecting a ventricular rate greater than 90 beats per minute (bpm). In particular, RVR may be determined in response to detecting that the heart is in AF and has a ventricular rate greater than 90 bpm.

Providing a recommendation that the patient see a physician 410 may be included in the method 400. As illustrated, in response to determining that the patient has an RVR 406, the method 400 may include providing a recommendation that the patient see a physician 410. Providing the recommendation may mean that the patient's status, or condition, is outside of the capabilities for the system 100 to administer treatment.

As used herein, the term "physician" refers to a medical professional, such as a doctor, a nurse, or other appropriate clinician. The terms may be used interchangeably unless the context of use indicates otherwise.

The recommendation to see a physician may be provided to any suitable system or person. In one example, the recommendation may be provided to the patient. In another example, the recommendation may be provided to the physician through the system 100 or sent to another system accessible by the physician.

Determining whether the patient is stable or recovered 408 may be included in the method 400. As illustrated, in response to administering diuretic intervention 404, the method 400 may include determining whether the patient is stable or recovered 408.

Any suitable technique may be used to determine whether the patient is stable or recovered known to one of ordinary skill in the art having the benefit of the present disclosure. In some embodiments, a determination that the patient is stable or recovered may be based on sensor-based parameters. For example, a patient may be stable or recovered when all parameters in a particular set of sensor-based parameters return to a normal range. In some embodiments, a determination that the patient is stable or recovered may be based, additionally or alternatively, on a composite of sensor-based parameters. For example, a patient may be stable or recovered when a composite of sensor-based parameters is used to generate an HF risk, and the HF risk decreases to a low risk or medium risk level. In particular, a medium risk level may be sufficient when a patient is normally at a medium risk level when in a non-decompensated state. A medium risk level may be the lowest risk level some patients can achieve in response to available interventions. In some embodiments, a determination that the patient is stable or recovered is based on the HF risk returning to a low or medium risk level (depending on the patient) and a normalization of sensor-based parameters.

Determining whether the patient has acceptable kidney function 412 may be included in the method 400. As illustrated, in response to determining that the patient is not stable or recovered 408, the method 400 may include determining whether the patient has acceptable kidney function 412.

Any suitable technique may be used to determine whether the patient has acceptable kidney function known to one of ordinary skill in the art having the benefit of the present disclosure. In some embodiments, acceptable kidney function may be determined based on comparing a creatinine or estimated glomerular filtration rate (eGFR or GFR) to a corresponding threshold. For example, an eGFR greater than 25, 30, 35, or 40 ml/min/1.73 m$^2$ may be deemed to be acceptable kidney function. In some embodiments, a suitable technique for determining whether the patient has acceptable kidney function includes comparing a potassium (K+) level to a threshold. For example, a potassium level greater than or equal to 3.5 mmol/L or less than or equal to 5.5 mmol/L may be deemed to be acceptable kidney function. In other words, a potassium level less than 3.5 mmol/L or greater than 5.5 mmol/L may be deemed unacceptable.

As illustrated, in response to determining that the kidney function is not acceptable 412, the method 400 may include recommending that the patient see a physician or notifying a physician 410. Also, as illustrated, in response to determining that the kidney function is acceptable, the method 400 may include administering another diuretic intervention 414. Administering the diuretic intervention 414 may be the same or similar to administering the diuretic intervention 404.

Determining whether sensor-based parameters are acceptable 416 may be included in the method 400. As illustrated, in response to determining that the patient is stable or recovered 408, the method 400 may include determining whether certain sensor-based parameters are acceptable 416, for example, before optimizing cardiac function 450.

Any suitable technique for determining whether the sensor-based parameters are acceptable, such as before optimizing cardiac function, may be used known to one of ordinary skill in the art having the benefit of the present disclosure. In some embodiments, the sensor-based parameters may each be compared to a threshold. For example, sensor-based parameters including one or more of a creatinine, a blood pressure, and a CO parameter may be determined and compared to corresponding thresholds. In one example, an eGFR greater than 25, 30, 35, or 40 ml/min/1.73 m$^2$ may be deemed to be acceptable for a creatinine parameter. In another example, a systolic blood pressure (SBP) greater than 90 mmHg may be deemed to be acceptable for a blood pressure parameter. In a further example, a CO greater than 3 L/min may be deemed to be acceptable for a CO parameter. In a still further example, a CI may be used in addition to or as an alternative to CO. In particular, a CI greater than 2.5 L/min/m$^2$ may be deemed to be acceptable for a CO parameter.

Any suitable technique may be used to determine CO known to one of ordinary skill in the art having the benefit of the present disclosure. In some embodiments, CO may be determined based on oxygen perfusion.

A physician may be notified 418 in the method 400. As illustrated, in response to the sensor-based parameters not being acceptable 416, or not within acceptable ranges, the method 400 may include notifying a physician 418. In one example, the physician may be notified through the system 100 or sent to another system accessible by the physician.

In some embodiments, notifying a physician 418 may include a recommendation to the physician to adjust the thresholds or ranges of acceptable of sensor-based parameters for the particular patient. For example, sensor-based parameters may not be fully normalized in response to available intervention for some patients with comorbidities. Adjusting the thresholds or ranges of acceptable sensor-based parameters may allow the system 100 to administer treatment once adjusted.

In the illustrated embodiment, in response to administering another diuretic intervention 414, the method 400 may include determining whether the patient is stable or recovered 420. Determining whether the patient is stable or recovered 420 may be the same or similar to determining whether the patient is stable or recovered 408.

Administering renal function intervention 422 may be included in the method 400. As illustrated, in response to determining that the patient is not stable or recovered 420, the method 400 may include administering renal function intervention 422.

Any suitable technique for administering renal function intervention may be used known to one of ordinary skill in the art having the benefit of the present disclosure. In some embodiments, renal function intervention treatment may include at least one of decreasing chronic diuretic dosage or monitoring renal function using eGFR, for example, while administering diuretic intervention.

Cardiac function may be optimized 450 in the method 400. As illustrated, in response to determining that certain sensor-based parameters are acceptable 416, or within acceptable range, the method 400 may include optimizing cardiac function 450.

Any suitable technique for optimizing cardiac function may be used known to one of ordinary skill in the art having the benefit of the present disclosure. In some embodiments, optimizing cardiac function may include at least one of optimizing baseline drugs or changing drugs. For example, changing drugs may include changing ACEi or ARB to a combination of neprilysin inhibitor and ARB.

Figure 5:
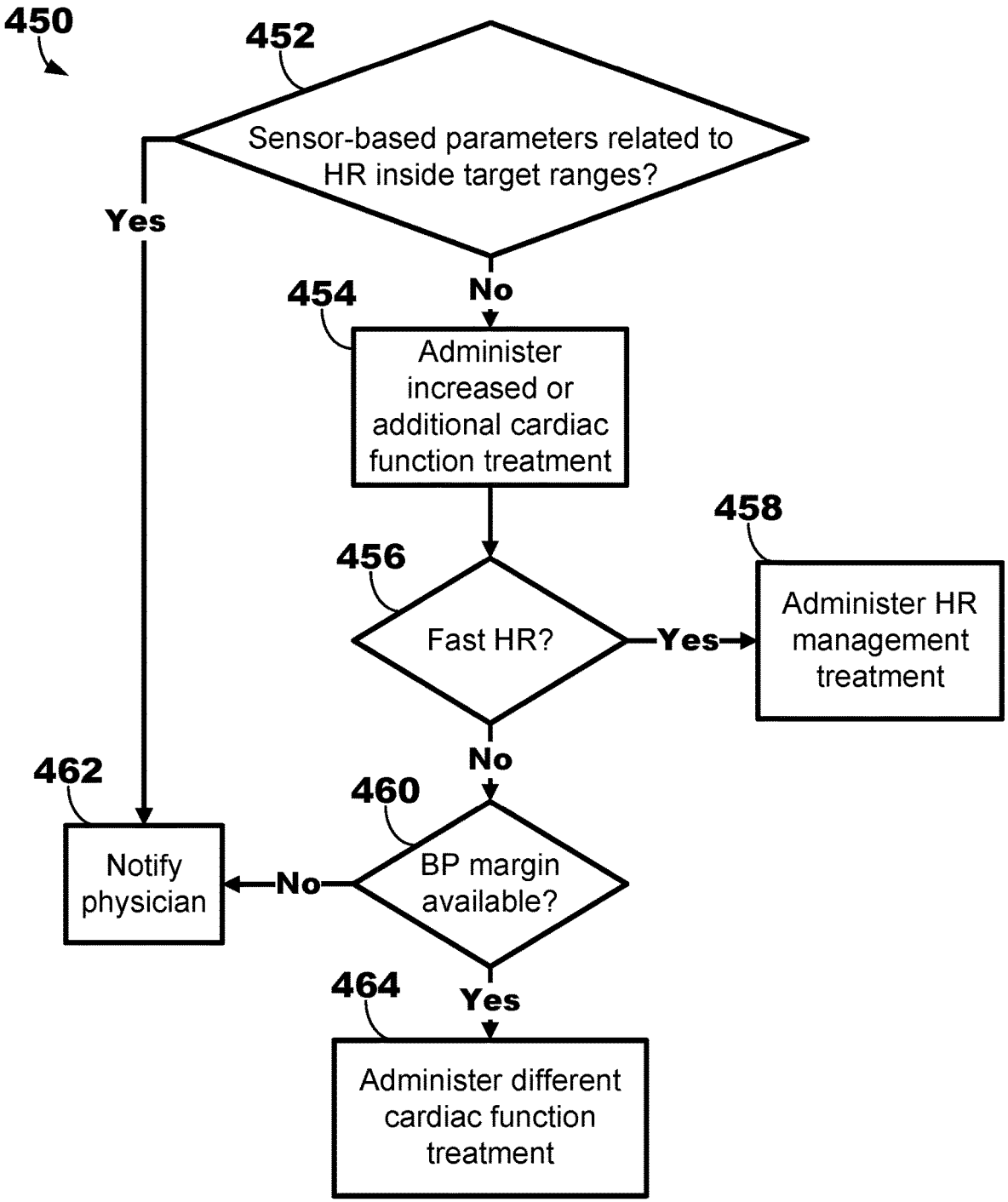
FIG. 5 shows a flow diagram that illustrates one example of a method of optimizing cardiac function usable in the method of FIG. 4, with the treatment management system of FIG. 1, or in the environment of FIG. 2.

FIG. 5 shows a flow diagram that illustrates one example of a method 450 of optimizing cardiac function usable in the method 400, with the system 100, or in the environment 200. The method 450 may include determining whether sensor-based parameters related to HR are inside corresponding target ranges 452. The method 450 may include notifying a physician 462, for example, in response to the sensor-based parameters related to HR are inside corresponding target ranges.

Any suitable technique for determining whether sensor-based parameters related to HR are inside target may be used known to one of ordinary skill in the art having the benefit of the present disclosure. In some embodiments, determining whether sensor-based parameters related to HR are acceptable includes comparing one or more HR parameters to corresponding thresholds. For example, one or more HR parameters selected from NHR, daytime resting HR, and HRV may be compared to corresponding thresholds. In some embodiments, an NHR less than or equal to 85 bpm may be deemed to be inside a target range. In some embodiments, a daytime resting HR less than or equal to 90 bpm may be deemed to be inside a target range. In some embodiments, an HRV less than or equal to 60 ms may be deemed to be inside a target range.

Administering increased or additional cardiac function treatment 454 may be included in method 450. As illustrated, in response to determining that sensor-based parameters related to HR are not inside corresponding target ranges 452, or outside the corresponding target ranges, the method 450 may include administering increased or additional cardiac function treatment 454.

Any suitable technique may be used for administering increased or additional cardiac function treatment known to one of ordinary skill in the art having the benefit of the present disclosure. In some embodiments, administering increased or additional cardiac function treatment may include at least one of increasing beta blocker, adding digitalis, or both. In some embodiments, administering increased or additional cardiac function treatment may, additionally or alternatively, include at least one of adding hydralazine, adding nitrates, or adding both.

Determining whether the patient has a fast HR 456 may be determined in the method 450. As illustrated, in response to administering increased or additional cardiac function treatment 454, the method 450 may include determining whether the patient has a fast HR 456. The fast HR may be determined based on sensor-based parameters determined or generated by the system 100 or may be provided to the system 100 from another system.

Any suitable technique may be used to determine whether the patient has a fast HR known to one of ordinary skill in the art having the benefit of the present disclosure. In some embodiments, the fast HR may be determined using daytime resting HR. The system 100 may be used to track the activity level of the patient using a patient implantable sensor or patient wearable sensor. The system 100 may record HR, for example, only when the activity is below a particular threshold. The average of daytime resting HR during these periods of inactive time may be recorded. Daytime may be defined in any suitable manner, for example, using a nominal range from 8 a.m. to 10 p.m. or using a patient or physician defined window. The patient or physician defined window may be selected based on when the patient gets out of bed (beginning) and when the patient goes to bed (end).

Administering HR management treatment 458 may be included in the method 450. As illustrated, in response to determining that the patient has a fast HR 456, the method 450 may include administering HR management treatment 458.

Any suitable technique may be used to administer HR management treatment known to one of ordinary skill in the art having the benefit of the present disclosure. In some embodiments, administering HR management treatment may include adding ivabradine, a block of funny channel current (If) in the sinus node, to the treatment.

Determining whether a BP margin is available 460 may be included in the method 450. As illustrated, in response to determining that the patient does not have a fast HR 456, the method 450 may include determining whether a BP margin is available 460.

Any suitable technique may be used to determine whether a BP margin is available known to one of ordinary skill in the art having the benefit of the present disclosure. In general, having a BP margin indicates that the BP is high enough so that the patient may be able to tolerate a drop in BP, which may occur when certain medications are increased, without becoming symptomatic. In some embodiments, a BP margin may be determined based on comparing an SBP to a threshold. For example, an SBP greater than 90 mmHg may be deemed to have a sufficiently available BP margin. A sufficiently high SBP may mean, some administered drugs, such as betablockers, can be up titrated without causing hypotension. Some drugs, such as betablockers, may lower blood pressure.

In the illustrated embodiment, in response to determining that the BP margin is not available 460, the method 450 may include notifying a physician 462. In one example, the physician may be notified through the system 100 or sent to another system accessible by the physician. In some embodiments, notifying a physician 418 may include informing the physician that the patient may not have an available BP margin to change drugs.

Administering different cardiac function treatment 464 may be included in the method 450. As illustrated, in response to determining that a BP margin is available 460, the method 450 may include administering different cardiac function treatment 464.

Any suitable technique may be used to administer different cardiac function treatment known to one of ordinary skill in the art having the benefit of the present disclosure. In some embodiments, administering different cardiac function treatment may include changing drugs from ACEi or ARB to a combination of neprilysin inhibitor and ARB.

Figure 6:
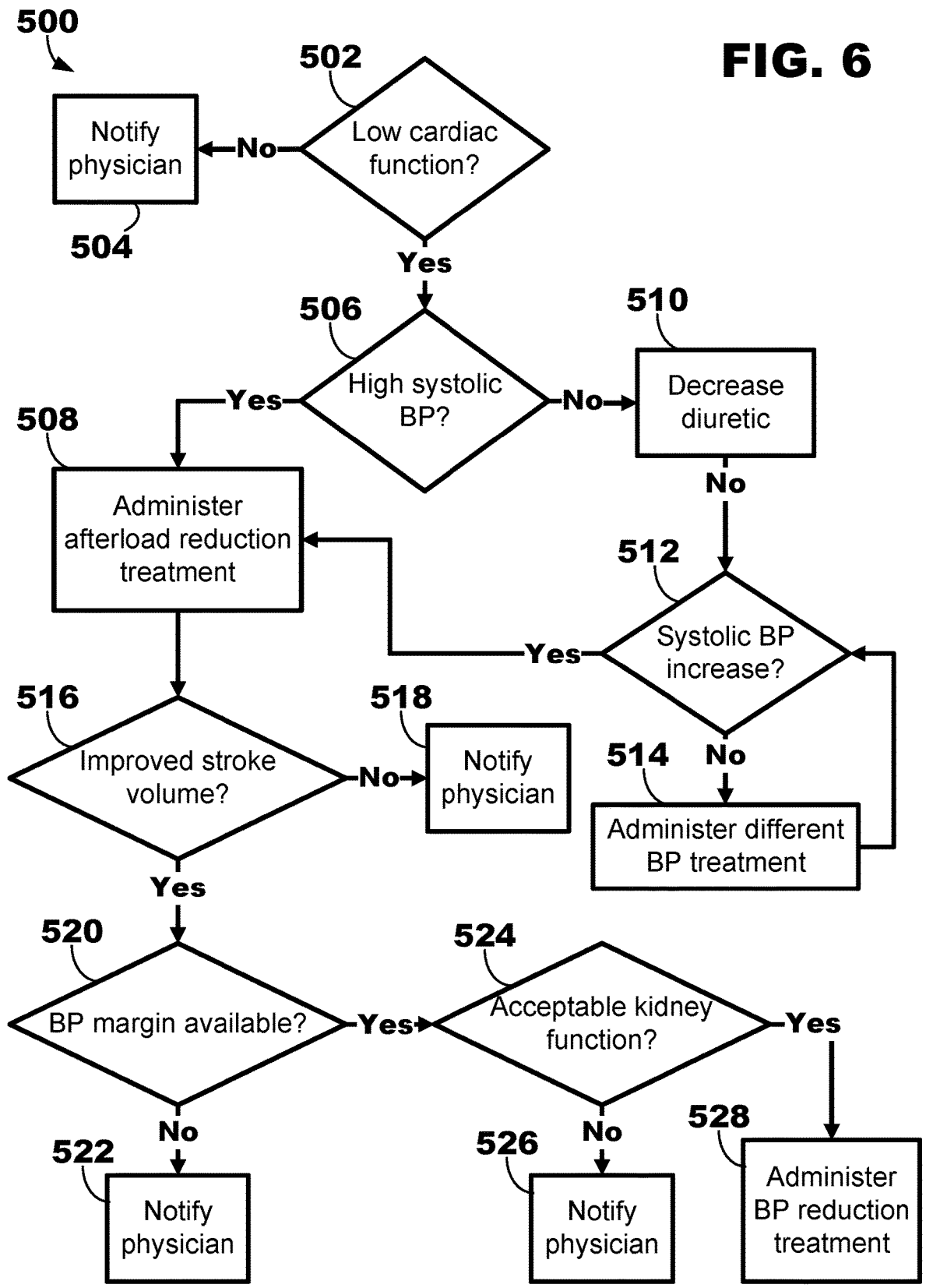
FIG. 6 shows a flow diagram that illustrates one example of a method guiding intervention with non-volume overload risk usable in the method of FIG. 3, with the treatment management system of FIG. 1, or in the environment of FIG. 2.

FIG. 6 shows one example of a method 500 of guiding intervention with non-volume overload risk usable in the method 300, with the system 100, or in the environment 200. The method 500 may include determining whether the patient has low cardiac function 502.

Any suitable technique may be used to determine whether the patient has low cardiac function known to one of ordinary skill in the art having the benefit of the present disclosure. In some embodiments, a determination that the patient has low cardiac function may be based on cardiac function, filling pressure, or both. For example, a patient may be deemed to have low cardiac function in response to having a low cardiac output, a low filling pressure, or both. Suitable thresholds to determine whether the patient has low cardiac function may be determined based on each patient. In some embodiments, a patient exhibiting a decrease in CO of 20-25% compared to a CO in a compensated state may be considered to have low cardiac function. In some embodiments, a trend of decreasing CO may be used to indicate low cardiac function.

In the illustrated embodiment, in response to determining that the patient does not have low cardiac function 502, the method 500 may include notifying a physician 504. In one example, the physician may be notified through the system 100 or sent to another system accessible by the physician. In some embodiments, notifying a physician 504 may include informing the physician that the patient's status, or condition, is outside of the capabilities for the system 100 to administer treatment. For example, the cause of risk may not be HF related.

Determining whether the patient has a high SBP 506 may be included in the method. As illustrated, in response to determining that the patient has low cardiac function 502, the method 500 may include determining whether the patient has a high SBP 506.

Any suitable technique may be used to determine whether the patient has a high SBP known to one of ordinary skill in the art having the benefit of the present disclosure. In some embodiments, the SBP may be compared to a corresponding threshold. For example, an SBP greater than 110 bpm may be deemed to be high.

Administering afterload reduction treatment 508 may be included in the method 500. As illustrated, in response to determining that the patient has high SBP 506, the method 500 may include administering afterload reduction treatment 508.

Any suitable technique may be used to administer afterload reduction treatment known to one of ordinary skill in the art having the benefit of the present disclosure. In some embodiments, administering afterload reduction treatment includes increasing or adding one or more of the following drugs: ACEi, ARB, and a combination of neprilysin inhibitor and ARB.

Decreasing administered diuretic 510 may be included in the method 500. As illustrated, in response to determining that the patient does not have high SBP 506, the method 500 may decrease administered diuretic 510.

Determining whether the patient has an increased SBP 512 may be included in the method 500. As illustrated, in response to decreasing administered diuretic 510, the method 500 may include determining whether the patient has an increased SBP 512.

Any suitable technique may be used to determine whether the patient has an increased SBP known to one of ordinary skill in the art having the benefit of the present disclosure. In some embodiments, the SBP after administering decreased diuretic may be compared to the SBP before administering decreased diuretic to determine whether the SBP has increased.

Administering a different BP treatment 514 may be included in the method 500. As illustrated, in response to determining that the SBP has not increased 512, the method 500 may include administering a different BP treatment 514.

Any suitable technique may be used to administer different BP treatment known to one of ordinary skill in the art having the benefit of the present disclosure. In some embodiments, beta blockers may be used. For example, a calcium channel blocker class of drugs may be used.

In the illustrated embodiment, in response to administering different BP treatment 514, the method 500 may include returning to determining whether the SBP has increased 512. Also, as illustrated, in response to determining that the SBP has increased 512, the method 500 may include administering afterload reduction treatment 508.

Determining whether the patient has improved SV 516 may be included in the method 500. As illustrated, in response to administering afterload reduction treatment 508, the method 500 may include determining whether the patient has improved SV 516.

Any suitable technique may be used to determine whether the patient has improved SV known to one of ordinary skill in the art having the benefit of the present disclosure. In some embodiments, the SV after administering afterload reduction treatment may be compared to the SV before administering afterload reduction treatment to determine whether the SV has increased (e.g., improved).

In the illustrated embodiment, in response to determining SV has not improved 516, the method 500 may include notifying a physician 518. Notifying a physician 518 may be the same or similar to notifying a physician 504.

Determining whether a BP margin is available 520 may be included in the method 500. As illustrated, in response to determining that the patient has improved SV 516, the method 500 may include determining whether the patient has a BP margin available 520. Determining whether the patient has a BP margin available 520 may be the same or similar to determining whether the patient has a BP margin available 460 (FIG. 5). It may be beneficial to lower BP when a BP margin is available.

In the illustrated embodiment, in response to determining that the patient does not have a BP margin available 520, the method 500 may include notifying a physician 522. Notifying a physician 522 may be the same or similar to notifying a physician 504.

Determining whether the patient has acceptable kidney function 524 may be included in the method 500. As illustrated, in response to determining that the patient has a BP margin available 520, the method 500 may include determining whether the patient has acceptable kidney function 524. Determining whether the patient has acceptable kidney function 524 may be the same or similar to determine whether the patient has acceptable kidney function 412 (FIG. 4). It may be beneficial to lower BP when kidney function is acceptable.

In the illustrated embodiment, in response to determining that the patient does not have acceptable kidney function 524, the method 500 may include notifying a physician 526. Notifying a physician 526 may be the same or similar to notifying a physician 504.

Administering BP reduction treatment 528 may be included in the method 500. As illustrated in response to determining that the patient has acceptable kidney function 524, the method 500 may include administering BP reduction treatment 528.

Any suitable technique may be used to administer BP reduction treatment known to one of ordinary skill in the art having the benefit of the present disclosure. In some embodiments, administering BP reduction treatment may include adding one or more of the following drugs: beta blocker, ACEi, and ARB. In general, any drug that lowers BP may be used.

ILLUSTRATIVE EMBODIMENTS

While the present disclosure is not so limited, an appreciation of various aspects of the disclosure will be gained through a discussion of the specific illustrative embodiments provided below, which provide guided intervention based on volume overload or non-volume overload. Various modifications of the illustrative embodiments, as well as additional embodiments of the disclosure, will become apparent herein.

In illustrative Embodiment A1, a method for heart failure management comprises:
receiving an alert indicative of a worsening heart failure score or status for a patient;
monitoring sensor-based parameters in response to receiving the alert;
determining whether the monitored sensor-based parameters indicate volume overload;
administering volume overload intervention in response to the monitored sensor-based parameters indicating volume overload; and
administering non-volume overload intervention in response to the monitored sensor-based parameters not indicating volume overload.

Some embodiments relate to administering volume overload intervention, for example, after a diuretic has been administered.

In illustrative Embodiment A2, a method comprises the method according to Embodiment A1, wherein administering volume overload intervention comprises administering treatment to optimize cardiac function in response to determining that the monitored sensor-based parameters are within corresponding acceptable ranges after administering at least one treatment for volume overload intervention.

In illustrative Embodiment A3, a method comprises the method according to Embodiment A2, wherein optimizing cardiac function comprises administering increased or additional cardiac function treatment in response to monitored sensor-based parameters related to heart rate being outside of corresponding target ranges.

In illustrative Embodiment A4, a method comprises the method according to Embodiment A3, wherein optimizing cardiac function further comprises:
determining whether the monitored sensor-based parameters are indicative of a fast heart rate after administering the increased or additional cardiac function treatment; and
administering heart rate management treatment in response to determining that the monitored sensor-based parameters are indicative of the fast heart rate.

In illustrative Embodiment A5, a method comprises the method according to Embodiment A4, wherein optimizing cardiac function further comprises:
determining whether a blood pressure margin is available in response to determining that the monitored sensor-based parameters are not indicative of the fast heart rate; and
administering a different cardiac function treatment than a previous cardiac function treatment in response to determining that the blood pressure margin is available.

Some embodiments relate to administering volume overload intervention, for example, to administer a diuretic.

In illustrative Embodiment A6, a method comprises the method according to any one of the preceding A Embodiments, wherein administering volume overload intervention based comprises:
determining whether the monitored sensor-based parameters are indicative of a heart rhythm in atrial fibrillation or in sinus rhythm;
determining whether the monitored sensor-based parameters are indicative of a rapid ventricular rate in response to determining that the monitored sensor-based parameters are indicative of the heart rhythm in atrial fibrillation;
administering diuretic intervention treatment in response to determining that the monitored sensor-based parameters are indicative of the heart rhythm in sinus rhythm or in response to determining that the monitored sensor-based parameters are not indicative of the rapid ventricular rate; and
providing a recommendation to see a physician in response to determining that the monitored sensor-based parameters are indicative of the rapid ventricular rate.

In illustrative Embodiment A7, a method comprises the method according to Embodiment A6, wherein administering volume overload intervention further comprises:
determining whether the patient is stable or recovered after administering the diuretic intervention treatment;
determining whether the patient has acceptable kidney function in response to determining that the patient is not stable or recovered;
administering a second diuretic intervention treatment in response to determining that the patient has acceptable kidney function and an acceptable potassium level; and
providing a recommendation to see a physician in response to determining that the patient does not have acceptable kidney function.

In illustrative Embodiment A8, a method comprises the method according to Embodiment A7, wherein administering volume overload intervention further comprises:
determining whether the patient is stable or recovered after administering the second diuretic intervention treatment; and
administering renal function intervention treatment in response to determining that the patient is not stable or recovered.

Some embodiments relate to administering non-volume overload intervention.

In illustrative Embodiment A9, a method comprises the method according to any one of the preceding A Embodiments, wherein administering non-volume overload intervention comprises:
determining whether the monitored sensor-based parameters are indicative of low cardiac function;
determining the patient has high systolic blood pressure in response to determining that the monitored sensor-based parameters are indicative of low cardiac function;
administering afterload reduction treatment in response to determining that the patient has high systolic blood pressure; and decreasing diuretic intervention treatment in response to determining that the patient does not have high systolic blood pressure.

In illustrative Embodiment A10, a method comprises the method according to Embodiment A9, wherein administering non-volume overload intervention further comprises:
determining whether systolic blood pressure increased after decreasing the diuretic intervention treatment;
administering a different blood pressure treatment in response to determining that the systolic blood pressure did not increase; and
administering afterload reduction treatment in response to determining that the systolic blood pressure increased.

In illustrative Embodiment A11, a method comprises the method according to Embodiment A9 or A10, wherein administering non-volume overload intervention further comprises:
determining whether the patient has improved stroke volume after administering the afterload reduction treatment;
determining whether a blood pressure margin is available in response to determining that the patient has improved stroke volume;
determining whether the patient has acceptable kidney function in response to determining that the blood pressure margin is available; and
administering blood pressure reduction treatment in response to determining that the patient has acceptable kidney function.

In illustrative Embodiment B 1, a computer-readable medium comprising instructions stored thereon, the instructions when executed by a processor cause the processor to perform the method according to any one of the A Embodiments.

Some embodiments relate to a heart failure management system to administer volume overload or non-volume overload intervention.

In illustrative Embodiment C1, a heart failure management system comprises:
one or more sensors to measure one or more sensor-based parameters selected from: impedance, resting heartrate, heartrate variability, nighttime heart rate, atrial fibrillation, rapid ventricular rate, activity, systolic blood pressure, and oxygen perfusion, cardiac output, and cardiac index; and
processing circuitry operably coupled to the one or more sensors, the processing circuitry configured to:
monitor sensor-based parameters in response to receiving indicative of a worsening heart failure score or status for a patient;
determine whether the monitored sensor-based parameters indicate volume overload;
administer volume overload intervention in response to the sensor-based parameters indicating volume overload; and
administer non-volume overload intervention in response to the monitored sensor-based parameters not indicating volume overload.

In illustrative Embodiment C2, a system comprises the system according to Embodiment C1, wherein to administer volume overload intervention, the processing circuitry is further configured to administer treatment to optimize cardiac function in response to determining that the monitored sensor-based parameters are within corresponding acceptable ranges.

In illustrative Embodiment C3, a system comprises the system according to Embodiment C2, wherein to optimize cardiac function, the processing circuitry is further configured to administer increased or additional cardiac function treatment in response to the monitored sensor-based parameters being outside of corresponding target ranges.

In illustrative Embodiment C4, a system comprises the system according to Embodiment C3, wherein to optimize cardiac function, the processing circuitry is further configured to:
determine whether the monitored sensor-based parameters are indicative of a fast heart rate after administering the increased or additional cardiac function treatment; and
administer heart rate management treatment in response to determining that the monitored sensor-based parameters are indicative of the fast heart rate.

In illustrative Embodiment C5, a system comprises the system according to Embodiment C4, wherein to optimize cardiac function, the processing circuitry is further configured to:
determine whether a blood pressure margin is available in response to determining that the monitored sensor-based parameters are not indicative of the fast heart rate; and
administer a different cardiac function treatment than a previous cardiac function treatment in response to determining that the blood pressure margin is available.

In illustrative Embodiment C6, a system comprises the system according to any one of the preceding C Embodiments, wherein to administer non-volume overload intervention, the processing circuitry is further configured to:
determine whether the monitored sensor-based parameters are indicative of low cardiac function;
determine the patient has high systolic blood pressure in response to determining that the monitored sensor-based parameters are indicative of low cardiac function;
administer afterload reduction treatment in response to determining that the patient has high systolic blood pressure; and
decrease diuretic intervention treatment in response to determining that the patient does not have high systolic blood pressure.

In illustrative Embodiment C7, a system comprises the system according to Embodiment C6, wherein to administer non-volume overload intervention, the processing circuitry is further configured to:
determine whether systolic blood pressure increased after decreasing the diuretic intervention treatment;
administer a different blood pressure treatment in response to determining that the systolic blood pressure did not increase; and
administer afterload reduction treatment in response to determining that the systolic blood pressure increased.

In illustrative Embodiment C8, a system comprises the system according to Embodiment C6 or C7, wherein to administer non-volume overload intervention, the processing circuitry is further configured to:
determine whether the patient has improved stroke volume after administering the afterload reduction treatment;
determine whether a systolic blood pressure margin is available in response to determining that the patient has improved stroke volume;
determine whether the patient has acceptable kidney function in response to determining that the systolic blood pressure margin is available; and administer blood pressure reduction treatment in response to determining that the patient has acceptable kidney function.

In illustrative Embodiment C9, a system comprises the system according to any one of the preceding C Embodiments, wherein to administer volume overload intervention, the processing circuitry is configured to perform the method according to any one of Embodiments A6-A8.

Thus, various embodiments of intervention for heart failure management are disclosed. Although reference is made herein to the accompanying set of drawings that form part of this disclosure, one of at least ordinary skill in the art will appreciate that various adaptations and modifications of the embodiments described herein are within, or do not depart from, the scope of this disclosure. For example, aspects of the embodiments described herein may be combined in a variety of ways with each other. Therefore, it is to be understood that, within the scope of the appended claims, the claimed invention may be practiced other than as explicitly described herein.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

All references and publications cited herein are expressly incorporated herein by reference in their entireties for all purposes, except to the extent any aspect directly contradicts this disclosure.

All scientific and technical terms used herein have meanings commonly used in the art unless otherwise specified. The definitions provided herein are to facilitate understanding of certain terms used frequently herein and are not meant to limit the scope of the present disclosure.

Unless otherwise indicated, all numbers expressing feature sizes, amounts, and physical properties used in the specification and claims may be understood as being modified either by the term "exactly" or "about." Accordingly, unless indicated to the contrary, the numerical parameters set forth in the foregoing specification and attached claims are approximations that can vary depending upon the desired properties sought to be obtained by those skilled in the art utilizing the teachings disclosed herein or, for example, within typical ranges of experimental error.

The recitation of numerical ranges by endpoints includes all numbers subsumed within that range (e.g. 1 to 5 includes 1, 1.5, 2, 2.75, 3, 3.80, 4, and 5) and any range within that range. Herein, the terms "up to" or "no greater than" a number (e.g., up to 50) includes the number (e.g., 50), and the term "no less than" a number (e.g., no less than 5) includes the number (e.g., 5).

The terms "coupled" or "connected" refer to elements being attached to each other either directly (in direct contact with each other) or indirectly (having one or more elements between and attaching the two elements). Either term may be modified by "operatively" and "operably," which may be used interchangeably, to describe that the coupling or connection is configured to allow the components to interact to carry out functionality.

As used herein, the term "configured to" may be used interchangeably with the terms "adapted to" or "structured to" unless the content of this disclosure clearly dictates otherwise.

What is claimed is:

1. A method for heart failure management comprising:
   receiving an alert indicative of a worsening heart failure score or status for a patient;
   monitoring sensor-based parameters in response to receiving the alert;
   determining whether the monitored sensor-based parameters indicate volume overload;
   administering volume overload intervention in response to the monitored sensor-based parameters indicating volume overload; and
   administering non-volume overload intervention in response to the monitored sensor-based parameters not indicating volume overload.

2. The method according to claim 1, wherein administering volume overload intervention comprises administering treatment to optimize cardiac function in response to determining that the monitored sensor-based parameters are within corresponding acceptable ranges after administering at least one treatment for volume overload intervention.

3. The method according to claim 2, wherein optimizing cardiac function comprises administering increased or additional cardiac function treatment in response to monitored sensor-based parameters related to heart rate being outside of corresponding target ranges.

4. The method according to claim 3, wherein optimizing cardiac function further comprises:
   determining whether the monitored sensor-based parameters are indicative of a fast heart rate after administering the increased or additional cardiac function treatment; and
   administering heart rate management treatment in response to determining that the monitored sensor-based parameters are indicative of the fast heart rate.

5. The method according to claim 4, wherein optimizing cardiac function further comprises:
   determining whether a blood pressure margin is available in response to determining that the monitored sensor-based parameters are not indicative of the fast heart rate; and administering a different cardiac function treatment than a previous cardiac function treatment in response to determining that the blood pressure margin is available.

6. The method according to claim 1, wherein administering volume overload intervention comprises:
   determining whether the monitored sensor-based parameters are indicative of a heart rhythm in atrial fibrillation or in sinus rhythm;
   determining whether the monitored sensor-based parameters are indicative of a rapid ventricular rate in response to determining that the monitored sensor-based parameters are indicative of the heart rhythm in atrial fibrillation;
   administering diuretic intervention treatment in response to determining that the monitored sensor-based parameters are indicative of the heart rhythm in sinus rhythm or in response to determining that the monitored sensor-based parameters are not indicative of the rapid ventricular rate; and
   providing a recommendation to see a physician in response to determining that the monitored sensor-based parameters are indicative of the rapid ventricular rate.

7. The method according to claim 6, wherein administering volume overload intervention further comprises:
   determining whether the patient is stable or recovered after administering the diuretic intervention treatment;
   determining whether the patient has acceptable kidney function in response to determining that the patient is not stable or recovered;
   administering a second diuretic intervention treatment in response to determining that the patient has acceptable kidney function and an acceptable potassium level; and
   providing a recommendation to see a physician in response to determining that the patient does not have acceptable kidney function.

8. The method according to claim 7, wherein administering volume overload intervention further comprises:
   determining whether the patient is stable or recovered after administering the second diuretic intervention treatment; and
   administering renal function intervention treatment in response to determining that the patient is not stable or recovered.

9. The method according to claim 1, wherein administering non-volume overload intervention comprises:
   determining whether the monitored sensor-based parameters are indicative of low cardiac function;
   determining the patient has high systolic blood pressure in response to determining that the monitored sensor-based parameters are indicative of low cardiac function;
   administering afterload reduction treatment in response to determining that the patient has high systolic blood pressure; and
   decreasing diuretic intervention treatment in response to determining that the patient does not have high systolic blood pressure.

10. The method according to claim 9, wherein administering non-volume overload intervention further comprises:
    determining whether systolic blood pressure increased after decreasing the diuretic intervention treatment;
    administering a different blood pressure treatment in response to determining that the systolic blood pressure did not increase; and
    administering afterload reduction treatment in response to determining that the systolic blood pressure increased.

11. The method according to claim 9, wherein administering non-volume overload intervention further comprises:
    determining whether the patient has improved stroke volume after administering the afterload reduction treatment;
    determining whether a blood pressure margin is available in response to determining that the patient has improved stroke volume;
    determining whether the patient has acceptable kidney function in response to determining that the blood pressure margin is available; and
    administering blood pressure reduction treatment in response to determining that the patient has acceptable kidney function.

12. A computer-readable medium comprising instructions stored thereon, the instructions when executed by a processor cause the processor to perform the method according to claim 1.

13. A heart failure management system comprising:
    one or more sensors to measure one or more sensor-based parameters selected from: impedance, resting heartrate, heartrate variability, nighttime heart rate, atrial fibrillation, rapid ventricular rate, activity, systolic blood pressure, and oxygen perfusion, cardiac output, and cardiac index; and
    processing circuitry operably coupled to the one or more sensors, the processing circuitry configured to:
      monitor sensor-based parameters in response to receiving an alert indicative of a worsening heart failure score or status for a patient;
      determine whether the monitored sensor-based parameters indicate volume overload;
      administer volume overload intervention in response to the sensor-based parameters indicating volume overload; and
      administer non-volume overload intervention in response to the monitored sensor-based parameters not indicating volume overload.

14. The system according to claim 13, wherein to administer volume overload intervention, the processing circuitry is further configured to administer treatment to optimize cardiac function in response to determining that the monitored sensor-based parameters are within corresponding acceptable ranges.

15. The system according to claim 14, wherein to optimize cardiac function, the processing circuitry is further configured to administer increased or additional cardiac function treatment in response to the monitored sensor-based parameters being outside of corresponding target ranges.

16. The system according to claim 15, wherein to optimize cardiac function, the processing circuitry is further configured to:
    determine whether the monitored sensor-based parameters are indicative of a fast heart rate after administering the increased or additional cardiac function treatment; and
    administer heart rate management treatment in response to determining that the monitored sensor-based parameters are indicative of the fast heart rate.

17. The system according to claim 16, wherein to optimize cardiac function, the processing circuitry is further configured to:
    determine whether a blood pressure margin is available in response to determining that the monitored sensor-based parameters are not indicative of the fast heart rate; and administer a different cardiac function treatment than a previous cardiac function treatment in response to determining that the blood pressure margin is available.

18. The system according to claim 13, wherein to administer non-volume overload intervention, the processing circuitry is further configured to:
   determine whether the monitored sensor-based parameters are indicative of low cardiac function;
   determine the patient has high systolic blood pressure in response to determining that the monitored sensor-based parameters are indicative of low cardiac function;
   administer afterload reduction treatment in response to determining that the patient has high systolic blood pressure; and
   decrease diuretic intervention treatment in response to determining that the patient does not have high systolic blood pressure.

19. The system according to claim 18, wherein to administer non-volume overload intervention, the processing circuitry is further configured to:
   determine whether systolic blood pressure increased after decreasing the diuretic intervention treatment;
   administer a different blood pressure treatment in response to determining that the systolic blood pressure did not increase; and
   administer afterload reduction treatment in response to determining that the systolic blood pressure increased.

20. The system according to claim 18, wherein to administer non-volume overload intervention, the processing circuitry is further configured to:
   determine whether the patient has improved stroke volume after administering the afterload reduction treatment;
   determine whether a systolic blood pressure margin is available in response to determining that the patient has improved stroke volume;
   determine whether the patient has acceptable kidney function in response to determining that the systolic blood pressure margin is available; and
   administer blood pressure reduction treatment in response to determining that the patient has acceptable kidney function.

* * * * *